United States Patent
Tanzio et al.

(10) Patent No.: US 9,790,179 B2
(45) Date of Patent: *Oct. 17, 2017

(54) PROCESSES FOR RECOVERING VALUABLE COMPONENTS FROM A CATALYTIC FAST PYROLYSIS PROCESS

(71) Applicant: Anellotech, Inc., Pearl River, NY (US)

(72) Inventors: Michael Tanzio, Cherry Hill, NJ (US); Charles M. Sorensen, Jr., Haverstraw, NY (US); Marc E. Schneidkraut, New York, NY (US); Jeffrey P. Whiting, Goshen, VT (US)

(73) Assignee: Anellotech, Inc., Pearl River, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/789,801

(22) Filed: Jul. 1, 2015

(65) Prior Publication Data

US 2016/0002162 A1 Jan. 7, 2016

Related U.S. Application Data (60) Provisional application No. 62/019,881, filed on Jul. 1, 2014.

(51) Int. Cl.

| | | |
|---|---|---|
| *C07D 209/08* | (2006.01) |
| *C07C 37/70* | (2006.01) |
| *C07D 307/79* | (2006.01) |
| *C07C 209/86* | (2006.01) |
| *C10K 1/08* | (2006.01) |
| *C10L 1/02* | (2006.01) |
| *C10L 1/04* | (2006.01) |
| *C10B 57/06* | (2006.01) |
| *C10G 1/08* | (2006.01) |
| *C10G 1/10* | (2006.01) |
| *C10G 3/00* | (2006.01) |

(52) U.S. Cl.
CPC ............ *C07D 209/08* (2013.01); *C07C 37/70* (2013.01); *C07C 209/86* (2013.01); *C07D 307/79* (2013.01); *C10B 57/06* (2013.01); *C10G 1/08* (2013.01); *C10G 1/10* (2013.01); *C10G 3/42* (2013.01); *C10K 1/085* (2013.01); *C10L 1/02* (2013.01); *C10L 1/04* (2013.01); *C10G 2400/30* (2013.01); *Y02E 50/14* (2013.01); *Y02P 30/20* (2015.11)

(58) Field of Classification Search
CPC .............................. C07D 209/08; C07C 37/70
See application file for complete search history.

(56) References Cited

U.S. PATENT DOCUMENTS

| | | |
|---|---|---|
| 2,400,802 A | 5/1946 | Arnold |
| 2,442,060 A | 5/1948 | Shepardson |
| 3,789,077 A | 1/1974 | Kosseim et al. |
| 3,816,302 A | 6/1974 | Paret |
| 3,923,921 A | 12/1975 | Kohfeldt |
| 3,996,129 A | 12/1976 | Weith |
| 4,086,159 A | 4/1978 | Baxter et al. |
| 4,101,597 A | 7/1978 | Breckenridge |
| 4,528,412 A | 7/1985 | Steacy et al. |
| 4,599,478 A | 7/1986 | Kamisaka et al. |
| 5,225,072 A | 7/1993 | Vidueira et al. |
| 5,279,646 A | 1/1994 | Schwab |
| 6,004,452 A | 12/1999 | Ash et al. |
| 6,576,132 B2 | 6/2003 | Kurukchi et al. |
| 7,820,033 B2 | 10/2010 | Eng et al. |
| 8,080,698 B2 | 12/2011 | Eng et al. |
| 8,137,628 B2 | 3/2012 | Cheiky et al. |
| 8,277,643 B2 | 10/2012 | Huber et al. |
| 8,748,680 B2 | 6/2014 | Hogendoorn |
| 8,936,654 B2 | 1/2015 | Platon et al. |
| 2012/0152801 A1 | 6/2012 | Bozzano et al. |
| 2012/0165584 A1 | 6/2012 | Eng |
| 2012/0167452 A1 | 7/2012 | Platon et al. |
| 2013/0060070 A1 | 3/2013 | Huber et al. |
| 2013/0205651 A1 | 8/2013 | Wang et al. |
| 2013/0245351 A1 | 9/2013 | Al-Haji |
| 2013/0306557 A1 | 11/2013 | Moore et al. |

FOREIGN PATENT DOCUMENTS

| | | |
|---|---|---|
| EP | 011 8310 A2 | 9/1984 |
| WO | 2014079572 A1 | 5/2014 |

OTHER PUBLICATIONS

Torren R. Carlson et al: "Production of green aromatics and olefins by catayltic fast pyrolysis of wood sawdust", Energy and Environmental Science, vol. 4, No. 1, Jan. 1, 2011, p. 145.
Invitation to Pay Additional Fees for International Application No. PCT/US2015/038898 dated Oct. 13, 2015 by Authorized Officer Luca Bonomelli on behalf of the EPO as International Searching Authority.
International Search Report for International Application No. PCT/US2015/038898 dated Oct. 7, 2015 by Officer Patricia Deurinck on behalf of the EPO as International Searching Authority.
Written Opinion of the International Searching Authority for International Application No. PCT/US2015/038898 , dated Oct. 7, 2015 by Officer Patricia Deurinck on behalf of the EPO as International Searching Authority.
Huber George et al, "Synthesis of Transportation Fuels from Biomass: Chemistry, Catalysts, and Engineering," Chem. Rev. 106, (2006), pp. 4044-4098.

(Continued)

*Primary Examiner* — Shawquia Jackson
(74) *Attorney, Agent, or Firm* — Frank Rosenberg (57) ABSTRACT

Methods of separating products from the catalytic fast pyrolysis of biomass are described. In a preferred method, a portion of the products from a pyrolysis reactor are recovered and separated using a quench system and solvent contacting system that employs materials produced in the pyrolysis process.

28 Claims, 3 Drawing Sheets

(56) References Cited

OTHER PUBLICATIONS

Rezaei, Pouya Sirous et al, "Production of green aromatics and olefins by catalytic cracking of oxygenate compounds derived from biomass pyrolysis: A review" Applied Catalysis A: General, 469 (2014) 490-511.

PROCESSES FOR RECOVERING VALUABLE COMPONENTS FROM A CATALYTIC FAST PYROLYSIS PROCESS

RELATED APPLICATIONS

This application claims priority to U.S. Provisional Patent Application No. 62/019,881 filed Jul. 1, 2014.

INTRODUCTION

Since the beginning of the Industrial Age, human desires for travel and consumer goods have driven the ever increasing consumption of fossil fuels such as coal and oil, typically obtained from deep underground. The extraction of fossil fuels by mining and drilling has often been accompanied by environmental and political costs. Furthermore, as the more accessible sources of fossil fuels are being used up; this has led to the pursuit of more expensive extraction technologies such as fracking and deep sea drilling. Additionally, the consumption of fossil fuels causes higher levels of atmospheric carbon, typically in the form of carbon dioxide.

To reduce these problems, there have been extensive efforts made in converting biomass to fuels and other useful chemicals. Unlike fossil fuels, biomass is renewable and carbon-neutral; that is, biomass-derived fuels and chemicals do not lead to increased atmospheric carbon since the growth of biomass consumes atmospheric carbon. Much of the work on biomass has involved converting refined biomass including vegetable oils, starches, and sugars; however, since these types of refined biomass may alternatively be consumed as food, there is even a greater utility for converting non-food biomass such as agricultural waste (bagasse, straw, corn stover, corn husks, etc.), energy crops (like switch grass and saw grass), trees and forestry waste, such as wood chips and saw dust, waste from paper mills, plastic waste, recycled plastics or algae, in combination sometimes referred to as cellulosic biomass. This non-food biomass generally includes three main components: lignin, hemicellulose, and cellulose.

Generating fuels and chemicals from biomass requires specialized conversion processes different from conventional petroleum-based conversion processes due to the nature of the feedstock. High temperatures, solid feed, high concentrations of water, unusual separations, and oxygenated by-products are some of the features of biomass conversion that are distinct from those encountered in petroleum upgrading. Thus, despite extensive efforts, there are many challenges that must be overcome to efficiently produce chemicals from biomass.

It is well known that a variety of biomass-derived polymeric materials such as lignin, cellulose, and hemi-cellulose, can be pyrolyzed to produce mixtures of aromatics, olefins, CO, CO2, water, and other products. A particularly desirable form of pyrolysis is known as catalytic fast pyrolysis (CFP) that involves the conversion of biomass in a catalytic fluid bed reactor to produce a mixture of aromatics, olefins, and a variety of other materials. The aromatics include benzene, toluene, xylenes, (collectively BTX), and naphthalene, among other aromatics. The olefins include ethylene, propylene, and lesser amounts of higher molecular weight olefins. BTX aromatics have high value and are easily transported.

The raw effluent from a CFP process is a complex mixture that comprises aromatics, olefins, oxygenates, paraffins, $H_2$, $CH_4$, CO, $CO_2$, water, char, ash, coke, catalyst fines, and a host of other compounds. Separation and recovery of the various components from this complex mixture present challenges that, despite extensive and costly efforts, have not been solved satisfactorily.

Aromatics recovery from process streams has been an active area of research and development for many years, but past processes have not been developed to effectively handle the complex mixture produced in the CFP process. For example, Arnold in U.S. Pat. No. 2,400,802 describes a scheme for separating aromatics from other hydrocarbons with an aqueous solvent system at high pressure and temperatures, but does not address the presence of solids, oxygenates, or gases such as $CO_2$, CO, $H_2$, and light hydrocarbons. Paret in U.S. Pat. No. 3,816,302 discloses a process for solvent extraction of aromatics from mixtures using a solvent containing morpholine, but does not address the presence of solids, oxygenates, water, or gases such as $CO_2$, CO, and $H_2$. Weith et al. in U.S. Pat. No. 3,996,129 describe a process for separating gases from liquids in a process effluent comprising aromatics, but do not discuss oxygenates or solids separation. In U.S. Pat. No. 4,086,159, Baxter and Gurgiolo describe the extraction of aromatics from liquid mixtures containing high concentrations of aromatics, olefins, and aliphatic hydrocarbons using polyol solvents. They do not address solids separation or the handling of gases and oxygenates. Vidueira in U.S. Pat. No. 5,225,072 describes an extractive distillation with solvents that have a polar function such as hydroxyl, amino, cyano, carboxyl or nitro group, wherein the aromatics are separated from the solvent in a steam stripping step; but no mention is made of separation of solids, fixed gases, or oxygenates. In U.S. Pat. No. 4,528,412, Steacy discloses a process for dehydrocyclodimerization of C3-C4 paraffins to aromatics and recovering aromatics using a lean absorption liquid stream but also do not discuss solids or oxygenates separation or recovery.

Patents for the quench and recovery of materials from hydrocarbon cracking, such as U.S. Pat. No. 2,442,060 to Shepardson, describe processes for recovering and separating aromatics, but do not address the problems of catalyst, char, ash, coke, or oxygenates separation or recovery. Likewise, steam cracking process patents, such as U.S. Pat. No. 3,923,921 to Kohfeldt, disclose the quenching of the raw effluent and separation and recovery of aromatics, but do not address the problems of solids or oxygenates removal and recovery. In U.S. Pat. No. 4,599,478, Kamisaka et al. describe a process for manufacturing olefins by thermal cracking but without addressing the problem of oxygenates, catalyst, or other solids separation and recovery. Kurukchi, et al. in U.S. Pat. No. 6,576,132 disclose a process for treating quench water from a stream cracker so the water can be recycled by stripping organic compounds and filtering solids, but provide no information for oxygenate or catalyst separations and recovery. In U.S. Pat. No. 7,820,033, Eng, et al. describe a process for producing ethylene by cracking C4-C10 hydrocarbons but do not mention of separating solids or recovering oxygenates as products. U.S. Pat. No. 8,080,698 to Eng et al. similarly describes a dehydrogenation process for producing olefins but does not address catalyst, solids, char, ash, or oxygenate separation or recovery. Further, Eng et al., in U.S. Published Patent Appl. No. 2012/0165584, describes a system for producing olefins from hydrocarbons by cracking, quenching, and catalytic upgrading, but does not separate or recover aromatics or oxygenates. Moore et al. in U.S. Published Patent Appl. No. 2013/0306557 describe a liquid-liquid extraction process using a low density, low water solubility solvent to concentrate many byproducts of the bio-oil obtained from a fast pyrolysis process. Platon et al. in U.S. Pat. No. 8,936,654 describe a process for quenching a highly reactive biomass pyrolysis product with a hydrocarbon solvent that dilutes the pyrolysis oil to prevent the heaviest and most reactive portions from polycondensation and thermal degradation. The process is not applicable to catalytic pyrolysis products and water is not considered a suitable quench liquid as it forms a separate phase and does not dilute the reactive components.

Thus, despite extensive efforts, a need remains for improved processes for recovering and separating aromatic and oxygenate products produced from the product effluent of a catalytic pyrolysis process. The present invention provides recovery and separation processes that quenches the hot effluent, separates the complex product mixture, and recovers valuable components.

SUMMARY OF THE INVENTION

In a first aspect, the invention provides a method for producing aromatic chemicals from the product stream of a catalytic pyrolysis process, comprising: quenching the product stream with water; separating a first liquid product and a first vapor phase, recovering aromatics from the first vapor phase; and recovering oxygenates from the first liquid product. Preferably, the feed to the catalytic pyrolysis process comprises biomass. In some preferred embodiments, the temperature of the first vapor phase is from 10° C. to 200° C., or from 20° C. to 150° C., or from 30° C. to 100° C., or from 40° C. to 80° C., or from 50° C. to 70° C. In some embodiments, the first vapor phase is condensed to produce a second liquid phase and a second vapor phase from the first vapor phase. The second liquid may comprise at least 50%, or at least 65%, or at least 75%, or at least 85%, or from 65 to 99%, or from 75 to 95%, or from 80 to 92%, or from 85 to 90% by weight benzene plus toluene plus xylenes. In some embodiments, the second liquid phase comprises less than 5%, or less than 2%, or less than 1%, or less than 0.25%, or from 0.01 to 5%, or from 0.03 to 2%, or from 0.05 to 1% by weight oxygenates. The invention also includes a liquid phase produced by the inventive methods. In some embodiments, an organic stream comprising benzene, toluene, xylenes, or ethyl benzene, or some combination of these is fed to the quench unit.

The invention may comprise: condensing the first vapor phase and separating a second liquid phase and a second vapor phase; contacting the first vapor phase or second vapor phase or a combination of them with a contacting solvent to produce a third liquid phase and third vapor phase, and recovering aromatics from the second liquid phase and the third liquid phase. In some preferred embodiments, the contacting solvent comprises a liquid stream produced from biomass in the process; the contacting solvent may comprise a portion of the first liquid product or the second liquid phase (having the conventional meaning of a portion of the first liquid phase or a portion of the second liquid phase). A portion of the xylenes-rich stream can be used as the contacting solvent. In some preferred embodiment, the contacting solvent comprises (or consists essentially of) xylenes produced in the CFP process. Preferably, the first liquid product is separated into an organic fraction and an aqueous fraction; the aqueous fraction may comprise less than 10%, or less than 5%, or less than 3%, or less than 2%, or from 0.1 to 10%, or from 0.5 to 5%, or from 1 to 3% aromatics by weight; the aqueous stream may comprise less than 10%, or less than 5%, or less than 2%, or less than 1%, or from 0.05 to 10%, or from 0.1 to 5%, or from 0.5 to 3% oxygenates by weight; the organic stream may comprises at least 80%, at least 85%, at least 90%, or at least 95%, or from 90 to 99.8% aromatics by weight; the organic stream may comprise at least 40%, or at least 50%, or at least 60%, or from 40 to 90%, or from 50 to 80%, or from 60 to 70% naphthalene by weight; the organic stream may comprise less than 25%, or less than 15%, or less than 10%, or from 0.1 to 25%, or from 1 to 15%, or from 2 to 10% oxygenates by weight. The invention also includes any of the organic or aqueous liquid product streams produced from the methods described herein. In some embodiments, an organic liquid product stream produced from the methods of the invention may comprise at least 80% aromatics by mass, at least 40% polycyclic aromatics by mass, less than 25% monocyclic aromatics by mass, less than 25% oxygenates by mass, and less than 5% water by mass. In some embodiments, an organic liquid product stream produced from the methods of the invention may comprise from 60 to 99.8% aromatics by mass, from 40 to 90% polycyclic aromatics by mass, from 1 to 25% of monocyclic aromatics by mass, from 0.1 to 25% oxygenates by mass, and from 0.001 to 5% water by mass. Solids can be separated from the first liquid product and/or the aqueous phase.

In some preferred methods, the first liquid product is separated into an organic fraction and an aqueous fraction, and a portion of the organic phase is used as a contacting solvent. Preferred contacting solvents may have a boiling point greater than the boiling point of toluene. In some embodiments, a first liquid product is separated into an organic fraction and an aqueous fraction, and a portion of the aqueous fraction is used as quench water. Oxygenates may be recovered from the organic fraction. In some embodiments, at least 25%, or at least 50%, or at least 75%, or at least 90%, or at least 95% up to 100% of the water used in the quench liquid is water produced from biomass in the process. All or a portion of the aqueous stream can be cooled by heat exchange with a closed loop cooling water circuit; and/or may be cooled in a fin-fan air cooled heat exchanger.

In some preferred embodiments, a fluidization gas of the CFP process comprises a portion of the third vapor phase. A transport fluid used to transport biomass into the CFP reactor may comprise a portion of the third vapor phase. In some preferred embodiments, the first vapor is compressed before it is contacted with a contacting solvent.

In some particularly preferred embodiments, the raw CFP product stream passes through a venturi scrubber before entering a quench system. The raw product stream can be cooled before it passes into the venturi scrubber.

The CFP product stream may comprise: on a water-free and solids-free basis, the product stream of a catalytic pyrolysis process that is subjected to the inventive method comprises: 20 to 60%, or 25 to 55% or 30 to 50%, or at least 20%, or at least 25%, or at least 30% CO calculated on a mass % basis; or 10 to 50%, or 15 to 40%, or 20 to 35%, or at least 5%, or at least 10%, or at least 15%, or at least 20% $CO_2$ calculated on a mass % basis; or 0.1 to 2.0, or 0.2 to 1.5, or 0.3 to 0.75%, or at least 0.1%, or at least 0.2%, or at least 0.3%, or less than 10%, or less than 5%, or less than 1% $H_2$ calculated on a mass % basis; or 2 to 40, or 3 to 35 or 4 to 30%, or less than 40%, or less than 35%, or less than 30%, or less than 20% BTX calculated on a mass % basis; or 0.1 to 10, or 0.2 to 5, or 0.3 to 3%, or less than 5%, or less than 3%, or less than 2% oxygenates calculated on a mass % basis. In some embodiments, in the product stream, xylenes comprise at least 50%, or at least 60%, or at least 70%, or from 50 to 95%, or from 60 to 90%, or from 70 to 85% by weight.

The product stream from the catalytic pyrolysis process prior to any quenching or separation is termed the raw product and, in some embodiments, the recovery of benzene is greater than 75, or greater than 85, or greater than 90, or greater than 95, or greater than 97%, or from 75 to 99%, or from 90 to 98%, or from 95 to 97.5% of the benzene in the raw product, or the recovery of toluene is greater than 75, or greater than 85, or greater than 90, or greater than 95, or greater than 97%, or from 75 to 99%, or from 90 to 98.5%, or from 95 to 98% of the toluene in the raw product, or the recovery of xylenes is greater than 75, or greater than 85, or greater than 90, or greater than 92%, or from 75 to 99%, or from 85 to 98%, or from 90 to 93% of the xylenes in the raw product, or the recovery of the sum of ethylbenzene, styrene, and cumene is greater than 70, or greater than 80, or greater than 85, or greater than 89%, or from 70 to 99%, or from 85 to 95%, or from 88 to 90% of the ethylbenzene, styrene, and cumene in the raw product, or the recovery of naphthalene is greater than 85, or greater than 90, or greater than 95, or greater than 97, or greater than 99%, or from 85 to 100%, or from 95 to 99.9%, or from 99 to 99.8% of the naphthalene in the raw product, or any combination of these.

In some embodiments, the pH of the water used for the quench is controlled by the addition or removal of acids, bases, or buffer solutions. The aqueous stream may be fed to a stripper column to recover dissolved hydrocarbon materials.

In some embodiments, the water used for quench contains a corrosion inhibitor. In some preferred embodiments, the corrosion inhibitor is chosen from among amines, alkanolamines, imidazoline, phosphated ethoxylated alcohols/benzotriazole derivatives, or any other material that reduces metal corrosion. In some embodiments, a surfactant emulsion breaking compound is added to the first liquid products. In some preferred embodiments, the surfactant emulsion breaking compound is chosen from among amines, amyl-, butyl-, or nonyl resins, esters, polyols, polyol esters, sulfonates, or other material that breaks aqueous and organic emulsions, or some combination thereof.

In another aspect, the invention provides a method for producing aromatic chemicals from the product stream of a catalytic pyrolysis process, comprising: quenching the product stream with an organic quench fluid to form a quenched product stream, separating a first vapor phase and a first liquid phase from the quenched product stream, quenching the first vapor phase with water to form a quenched first vapor phase; separating a second vapor phase and a second liquid phase from the quenched first vapor phase, and recovering aromatics from the second vapor phase. In some preferred embodiments, the organic quench fluid comprises materials chosen from among diesel fuel, pyrolysis oil, pygas, jet fuel, heavy cycle oils, heavy coker gas oils, heavy visbreaking distillates, heavy thermal cracking distillates clarified catalytic cracking decant oils, vacuum gas oil, intermediate and heavy vacuum distillates, naphthenic oils, heavy hydrocracker distillates, heavy distillates from hydroprocessing, naphtha, C9+ organics, oxygenates, product streams from the CFP process, benzene, toluene, xylenes, ethyl benzene, styrene, cumene, propyl benzene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, naphthalene, methyl-naphthalene (e.g., 1-methyl naphthalene), anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, dimethyl-hydrindene, phenol, o-cresol, m-cresol, p-cresol, catechol, resorcinol, hydroquinone, 1-naphthol, 2-naphthol, benzofuran, or combinations thereof. Preferably, the organic quench fluid comprises at least 10, or at least 25, or at least 50, or at least 75, or at least 90% by weight of materials produced from biomass.

The invention also includes product stream such as can be produced by the inventive methods where the carbon in the product stream is derived from biomass. Thus, for example, the invention includes a product stream wherein the sum of benzene plus toluene comprises at least 80%, at least 85%, at least 90%, at least 92%, or from 80 to 99%, or from 85 to 97%, or from 90 to 95% by weight; or a product stream as wherein xylenes comprise at least 50%, or at least 60%, or at least 70%, or from 50 to 95%, or from 60 to 90%, or from 70 to 85% by weight.

In some aspects, the invention provides methods for producing aromatic chemicals from a catalytic pyrolysis product stream by recovering and separating at least a portion of the products into benzene-rich, toluene-rich, and xylenes-rich fractions, and returning a portion of the heavier or lighter hydrocarbon product to the product recovery system.

In preferred embodiments of the inventive method, apparatus, and/or system, the pyrolysis reactor contains a solid catalyst. The solid catalyst preferably comprises a zeolite, more preferably a zeolite and a metal and/or a metal oxide. The solid catalyst in the CFP reactor may comprise elements such as, for example, silicon, aluminum, titanium, vanadium, chromium, manganese, iron, cobalt, nickel, copper, zinc, gallium, platinum, palladium, silver, tin, phosphorus, sodium, potassium, magnesium, calcium, tungsten, zirconium, cerium, lanthanum, and combinations thereof. Additional catalyst materials or inert solids may also be present. In some preferred embodiments, the CFP reaction is catalyzed by a zeolite. In some embodiments, the zeolite comprises pore sizes in the range of 5.0 to 6.5 angstroms. In some preferred embodiments, the catalyst comprises ZSM5. In some preferred embodiments, the mass ratio of catalyst fed to the reactor to hydrocarbonaceous material fed to the reactor is between 0.1 and 40. In some preferred embodiments, the CFP reactor is a fluidized bed, circulating bed, or riser reactor. In some preferred embodiments, the temperature within the reactor is between 300 and 1000° C. In any of the inventive aspects, the pyrolysis step(s), (and/or any selected process step) may preferably be conducted at a pressure (absolute) of 30 atm or less, more preferably of less than 10 atm, in some embodiments less than 1 atm; and in some embodiments in the range of 0.1 to 10 atm.

The hydrocarbonaceous material fed to the reactor may comprise a biomass material; or plastic waste, recycled plastics, agricultural and municipal solid waste, food waste, animal waste, carbohydrates, or lignocellulosic materials; or the hydrocarbonaceous material can comprise xylitol, glucose, cellobiose, cellulose, hemi-cellulose, or lignin; or the hydrocarbonaceous material may comprise sugar cane bagasse, glucose, wood, or corn stover, or any of these materials in any combination. The hydrocarbonaceous material that is fed to the reactor typically comprises a solid hydrocarbonaceous material, often in the presence of a gas. In some preferred embodiments, the hydrocarbonaceous material is at least 90 mass % solids. In some lesser preferred embodiments the hydrocarbonaceous material could be only in the gas and/or a liquid or slurry phase. In some embodiments, a recycle stream, preferably an aqueous recycle stream, can be contacted with the hydrocarbonaceous material before the hydrocarbonaceous material is fed to the reactor.

The invention includes methods, apparatus, and systems (which comprise apparatus plus process streams (that is, fluid compositions) and may further be characterized by conditions such as temperature or pressure). Thus, any of the descriptions herein apply to the inventive methods, apparatus and systems.

Advantages of various aspects of the invention may include: increased yield, improved energy efficiency, isolation of especially desirable products and product mixtures, and reduced pollution.

Glossary

Aromatics—As used herein, the terms "aromatics" or "aromatic compound" are used to refer to a hydrocarbon compound or compounds comprising one or more aromatic groups such as, for example, single aromatic ring systems (e.g., benzyl, phenyl, etc.) and fused polycyclic aromatic ring systems (e.g. naphthyl, 1,2,3,4-tetrahydronaphthyl, etc.). Examples of aromatic compounds include, but are not limited to, benzene, toluene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, xylenes (e.g., p-xylene, m-xylene, o-xylene), naphthalene, methyl-naphthalene (e.g., 1-methyl naphthalene), anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, and dymethyl-hydrindene. Single-ring and/or higher ring aromatics may also be produced in some embodiments. Aromatics also include single and multiple ring compounds that contain heteroatom substituents, i.e., phenol, cresol, benzofuran, aniline, indole, etc.

Biomass—As used herein, the term "biomass" is given its conventional meaning in the art and is used to refer to any organic source of energy or chemicals that is renewable. Its major components can be: (1) trees (wood) and all other vegetation; (2) agricultural products and wastes (corn, fruit, garbage ensilage, etc.); (3) algae and other marine plants; (4) metabolic wastes (manure, sewage), and (5) cellulosic urban waste. Examples of biomass materials are described, for example, in Huber, G. W. et al, "Synthesis of Transportation Fuels from Biomass: Chemistry, Catalysts, and Engineering," Chem. Rev. 106, (2006), pp. 4044-4098.

Biomass is conventionally defined as the living and recently dead biological material that can be converted for use as fuel or for industrial production. The criterion for biomass is that the material should be recently participating in the carbon cycle so that the release of carbon in the combustion process results in no net increase averaged over a reasonably short period of time (for this reason, fossil fuels such as peat, lignite and coal are not considered biomass by this definition as they contain carbon that has not participated in the carbon cycle for a long time so that their combustion results in a net increase in atmospheric carbon dioxide). Most commonly, biomass refers to plant matter grown for use as biofuel, but it also includes plant or animal matter used for production of fibers, chemicals or heat. Biomass may also include biodegradable wastes or byproducts that can be burnt as fuel or converted to chemicals, including municipal wastes, green waste (the biodegradable waste comprised of garden or park waste, such as grass or flower cuttings and hedge trimmings), byproducts of farming including animal manures, food processing wastes, sewage sludge, black liquor from wood pulp or algae. Biomass excludes organic material which has been transformed by geological processes into substances such as coal, oil shale or petroleum. Biomass is widely and typically grown from plants, including miscanthus, spurge, sunflower, switchgrass, hemp, corn (maize), poplar, willow, sugarcane, and oil palm (palm oil) with the roots, stems, leaves, seed husks and fruits all being potentially useful. Processing of the raw material for introduction to the processing unit may vary according to the needs of the unit and the form of the biomass.

Catalysts—Catalyst components useful in the context of this invention can be selected from any catalyst known in the art, or as would be understood by those skilled in the art. Catalysts promote and/or effect reactions. Thus, as used herein, catalysts lower the activation energy (increase the rate) of a chemical process, and/or improve the distribution of products or intermediates in a chemical reaction (for example, a shape selective catalyst). Examples of reactions that can be catalyzed include: dehydration, dehydrogenation, isomerization, hydrogen transfer, aromatization, decarbonylation, decarboxylation, aldol condensation, molecular cracking and decomposition, and combinations thereof. Catalyst components can be considered acidic, neutral or basic, as would be understood by those skilled in the art.

For catalytic fast pyrolysis, particularly advantageous catalysts include those containing internal porosity selected according to pore size (e.g., mesoporous and pore sizes typically associated with zeolites), e.g., average pore sizes of less than about 100 Angstroms (Å), less than about 50 Å, less than about 20 Å, less than about 10 Å, less than about 5 Å, or smaller. In some embodiments, catalysts with average pore sizes of from about 5 Å to about 100 Å may be used. In some embodiments, catalysts with average pore sizes of between about 5.5 Å and about 6.5 Å, or between about 5.9 Å and about 6.3 Å may be used. In some cases, catalysts with average pore sizes of between about 7 Angstroms and about 8 Å, or between about 7.2 Å and about 7.8 Å may be used.

In some preferred embodiments of CFP, the catalyst may be selected from naturally occurring zeolites, synthetic zeolites and combinations thereof. In certain embodiments, the catalyst may be a ZSM-5 zeolite catalyst, as would be understood by those skilled in the art. Optionally, such a catalyst can comprise acidic sites. Other types of zeolite catalysts include: ferrierite, zeolite Y, zeolite beta, mordenite, MCM-22, ZSM-23, ZSM-57, SUZ-4, EU-1, ZSM-11, SAPO-31, SSZ-23, among others. In other embodiments, non-zeolite catalysts may be used; for example, WOx/ZrO2, aluminum phosphates, etc. In some embodiments, the catalyst may comprise a metal and/or a metal oxide. Suitable metals and/or oxides include, for example, nickel, palladium, platinum, titanium, vanadium, chromium, manganese, iron, cobalt, zinc, copper, gallium, and/or any of their oxides, among others. In some cases promoter elements chosen from among the rare earth elements, i.e., elements 57-71, cerium, zirconium or their oxides for combinations of these may be included to modify activity or structure of the catalyst. In addition, in some cases, properties of the catalysts (e.g., pore structure, type and/or number of acid sites, etc.) may be chosen to selectively produce a desired product.

Olefins—As used herein, the terms "olefin" or "olefin compound" (a.k.a. "alkenes") are given their ordinary meaning in the art, and are used to refer to any unsaturated hydrocarbon containing one or more pairs of carbon atoms linked by a double bond. Olefins include both cyclic and acyclic (aliphatic) olefins, in which the double bond is located between carbon atoms forming part of a cyclic (closed-ring) or of an open-chain grouping, respectively. In addition, olefins may include any suitable number of double bonds (e.g., monoolefins, diolefins, triolefins, etc.). Examples of olefin compounds include, but are not limited to, ethene, propene, allene (propadiene), 1-butene, 2-butene, isobutene (2 methyl propene), butadiene, and isoprene, among others. Examples of cyclic olefins include cyclopentene, cyclohexene, cycloheptene, among others. Aromatic compounds such as toluene are not considered olefins; however, olefins that include aromatic moieties are considered olefins, for example, benzyl acrylate or styrene.

Oxygenates—Oxygenates include any organic compound that contains at least one atom of oxygen in its structure such as alcohols (methanol, ethanol, etc.), acids (e.g. acetic acid, propionic acid, etc.), aldehydes (eg formaldehyde, acetaldehyde, etc), esters (eg methyl acetate, ethyl acetate, etc.), ethers (eg dimethyl ether, diethyl ether, etc.), aromatics with oxygen containing substituents (eg phenol, cresol, benzoic acid etc.), cyclic ethers, acids, aldehydes, and esters (e.g. furan, furfural, etc.), and the like.

Pyrolysis—As used herein, the terms "pyrolysis" and "pyrolyzing" are given their conventional meaning in the art and are used to refer to the transformation of a compound, e.g., a solid hydrocarbonaceous material, into one or more other substances, e.g., volatile organic compounds, gases and coke, by heat, preferably without the addition of, or in the absence of, $O_2$. Preferably, the volume fraction of $O_2$ present in a pyrolysis reaction chamber is 0.5% or less. Pyrolysis may take place with or without the use of a catalyst. "Catalytic pyrolysis" refers to pyrolysis performed in the presence of a catalyst, and may involve steps as described in more detail below. Example of catalytic pyrolysis processes are outlined, for example, in Huber, G. W. et al, "Synthesis of Transportation Fuels from Biomass: Chemistry, Catalysts, and Engineering," Chem. Rev. 106, (2006), pp. 4044-4098.

Recovery—The recovery of a component is the fraction (or percent) of that component that is present in the recovered product stream(s) compared to the amount of that component that is present in the reactor effluent stream. For example if 10 grams of product A is present in the raw effluent and 8.5 grams of product A is present in the recovered product stream(s), then the recovery of A is 8.5/10 or 0.85 (85%).

CFP Reaction Technology

Examples of apparatus and process conditions suitable for CFP are described in U.S. Pat. No. 8,277,643 of Huber et al. and in the US Patent Application 2013/0060070A1 of Huber et al. that are incorporated herein by reference. Conditions for CFP of biomass may include one or any combination of the following features (which are not intended to limit the broader aspects of the invention): a zeolite catalyst, a ZSM-5 catalyst; a zeolite catalyst comprising one or more of the following metals: titanium, vanadium, chromium, manganese, iron, cobalt, nickel, copper, zinc, gallium, platinum, palladium, silver, phosphorus, sodium, potassium, magnesium, calcium, tungsten, zirconium, cerium, lanthanum, and combinations thereof; a fluidized bed, circulating bed, or riser reactor; an operating temperature in the range of 300° to 1000° C.; and/or a solid catalyst-to-biomass mass feed ratio of between 0.1 and 40.

CFP Products—Components identified in the raw product stream include 1-methyl-2-cyclopropen-1-yl-benzene, 1-methylethyl-benzene, alpha-methylstyrene, 1-methylpropyl-benzene, 1-(2-furanyl)-ethanone, 1-(4-hydroxy-3,5-dimethoxyphenyl)-ethanone, 1,1-dimethyl-1h-indene, 1,1-dimethyl-cyclopropane, 1,2,3-trimethyl-benzene, 1,2,3-trimethylindene, 1,2-butadiene, 1,2-dihydro-naphthalene, 1,3,5-hexatriene, 1,3-bis(methylene)-cyclopentane, 1,3-cyclopentadiene, 1,3-dimethyl-1h-indene, 1,3-pentadiene, 1,4,6-trimethyl-naphthalene, 1,4-dimethyl-naphthalene, 1,4-pentadiene, 1,5-dihydroxy-1,2,3,4-tetrahydronaphthalene, 1,5-heptadien-3-yne, 1,5-hexadiyne, 1,6,7-trimethyl-naphthalene, 1-buten-3-yne, 1-ethenyl-2-methyl-benzene, 1-ethenyl-3-methylene-cyclopentene, 1-ethyl-2-methyl-benzene, 1-ethyl-4-methyl-benzene, 1-ethyl-cyclopentene, 1-ethyl-naphthalene, 1-indenol, 1-methyl-1,3-cyclopentadiene, 1-methyl-2-cyclopropen-1-yl-benzene, 1-methyl-9h-fluorene, 1-methyl-bicyclo[2.2.1]hept-2-ene, 1-methyl-cyclohexene, 1-methyl-cyclopentene, 1-methyl-indan, 1-methyl-naphthalene, 1-naphthalenol, 1-propenyl-benzene, 2-(1-methylethoxy)-ethanol, 2,3,6-trimethyl-phenol, 2,3-dihydro-4,7-dimethyl-1h-indene, 2,3-dihydro-benzofuran, 2,3-dimethyl-2-cyclopenten-1-one, 2,3-dimethyl-naphthalene, 2,5-dimethyl-furan, 2,5-dimethyl-phenol, 2,6-dimethyl-naphthalene, 2,6-dimethyl-phenol, 2-acetyl-5-norbornene, 2-butanone, 2-cyclopenten-1-one, 2-ethyl-4-methyl-phenol, 2-ethyl-furan, 2-ethyl-naphthalene, 2-ethyl-phenol, 2-hydroxyfluorene, 2-hydroxy-propanenitrile, 2-methyl-1,1'-biphenyl, 2-methyl-1,3-pentadiene, 2-methyl-1-butene, 2-methyl-1-naphthalenol, 2-methyl-1-pentene, 2-methyl-6-(2-propenyl)-phenol, 2-methyl-9h-fluorene, 2-methyl-benzofuran, 2-methyl-bicyclo[3.2.0]hept-2-ene, 2-methyl-bicyclo[3.2.0]hept-2-ene, 2-methyl-furan, 2-methyl-phenol (2-cresol), 2-methyl-propanal, 2-naphthalenol, 2-phenanthrenol, 2-propenal, 2-vinylfuran, 3,4-dimethylcyclopentene, 3,4-dimethyl-phenol, 3,5-dimethylcyclopentene, 3-methyl-1,1'-biphenyl, 3-methyl-1,2-benzenediol, 3-methyl-2-cyclopenten-1-one, 3-methyl-2-pentene, 3-methyl-bicyclo[3.3.0]oct-2-en-8-one, 3-methyl-cyclohexene, 3-methyl-cyclopentene, 3-methyl-furan, 3-methyl-phenanthrene, 3-methyl-phenol (3-cresol), 3-phenyl-2-propenal 4-cyclopentene-1,3-dione, 4-ethylcatechol, 4-hydroxy-3,5-dimethoxy-benzaldehyde, 4-hydroxy-3-methylbenzaldehyde, 4-methyl-1,2-benzenediol, 4-methyl-1,3-pentadiene, 4-methyl-dibenzofuran, 4-phenylbut-3-ene-1-yne, 5'-methyl-spiro[bicyclo[2.2.1]hept-5-ene-2,4'-[1,2]dioxolan]-3'-one, 5-norbornane-2-carboxaldehyde, 7-methyl-benzofuran, 9h-fluoren-9-ol, 9-methyl-anthracene, acetaldehyde, acetic acid, acetone, acetone, allene, alpha-methylstyrene, anthracene, benzene, benzofuran, bibenzyl, bicyclo[3.2.0]hepta-2,6-diene, biphenyl, bis-1,1'-(1-ethenyl-1,3-propanediyl)benzene, butanal, carbon dioxide, carbon monoxide, catechol, cis and trans-2-pentene, cis-2-butene, coumarin, cyclobutane, cyclohexene, cyclopentane, cyclopentene, dibenzofuran, ethane, ethyl-2-benzofuran, ethylbenzene, ethylene, fluorene, furan, hydrogen, hydroquinone, indane, isopropyl alcohol, isopropyl-benzene (cumene), mesitylene, methacrolein, methane, methyl vinyl ketone, methyl-cyclopentane, m-xylene, naphthalene, o-hydroxybiphenyl, o-xylene, phenol, p-hydroxybiphenyl, propanal, propene, propyl-benzene, p-xylene, quinoline, styrene, toluene, trans-2-butene, and water.

DETAILED DESCRIPTION OF THE INVENTION

Figure 1:
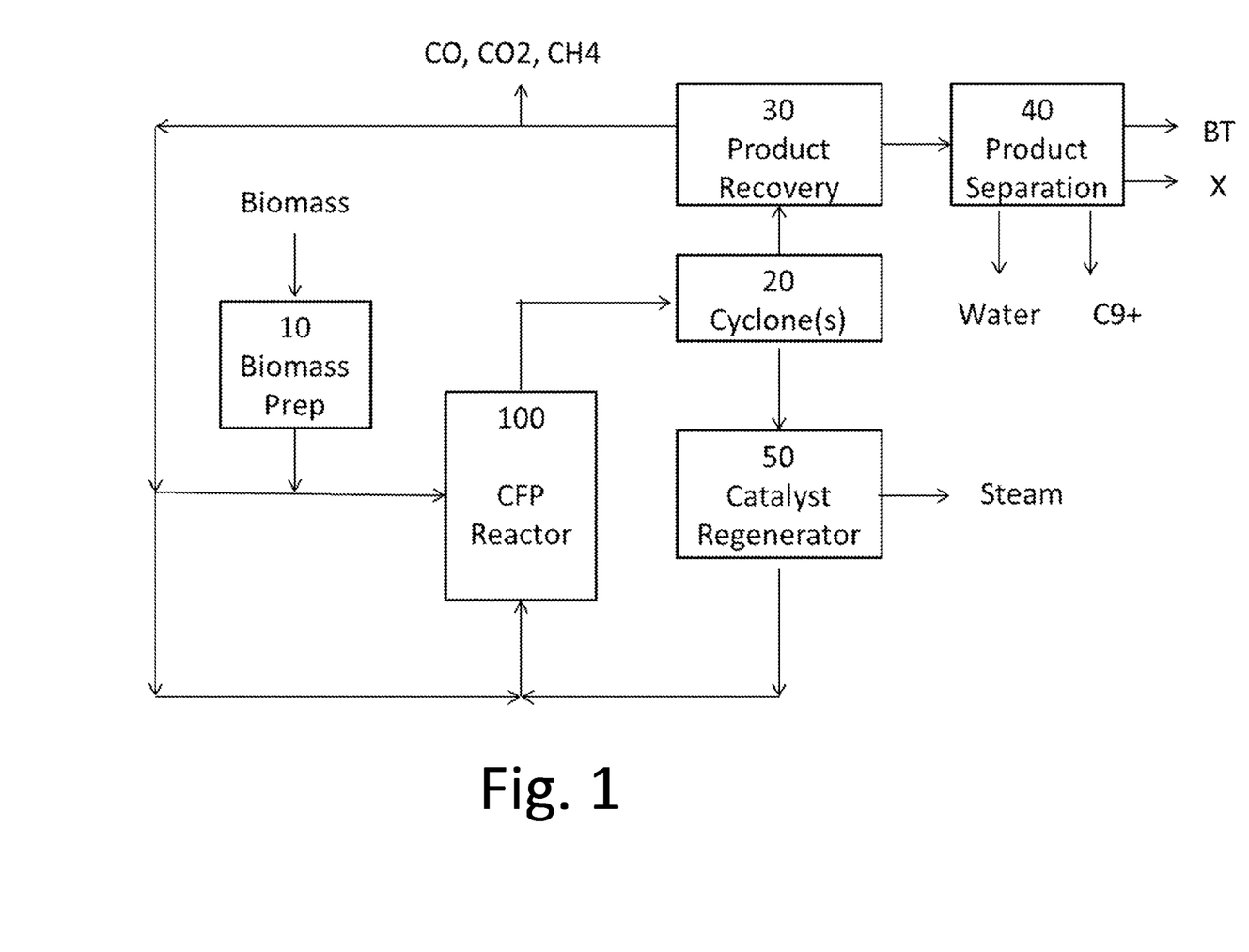
FIG. 1 illustrates a process for converting biomass into aromatics.

FIG. 1 shows an exemplary process for converting biomass to aromatics (BTX) and other components (C9+). Biomass is introduced and prepared in stage 10 by chipping, drying, grinding, or other processes, or some combination of these. The prepared biomass is introduced along with a recycle gas or transport fluid into the CFP reactor. The CFP reactor is a fluidized bed catalytic reactor that is fluidized by a portion of recycle gas or other fluid. The products from the CFP reactor are separated from some of the catalyst, minerals, or char that is carried along with the fluid stream in one or more cyclones. The catalyst from the cyclones and other catalyst removed from the reactor is regenerated in a catalyst regeneration system 50 in which the coke and char are combusted and the catalyst is cooled and returned to the reactor, or simply returned to the reactor. The raw fluid product is sent to a product recovery system 30 where the liquid products benzene, toluene, xylenes, naphthalenes, oxygenates, and other useful products are quenched, recovered, and separated from the non-condensable gases, i.e., CO, $CO_2$, $CH_4$, $H_2$, and light olefins and paraffins, and the water, char, coke, ash, and catalyst fines. A portion of the gases is purged, and a portion is optionally recycled for use in the CFP reactor. The crude mixture of BTX and other products is separated into various fractions in separation step 40 producing a water stream that can be recycled or sent to a water treatment system or otherwise utilized, a heavy fraction that contains C9+, oxygenates, and other materials, and various fractions of benzene, toluene, and xylenes.

Figure 2:
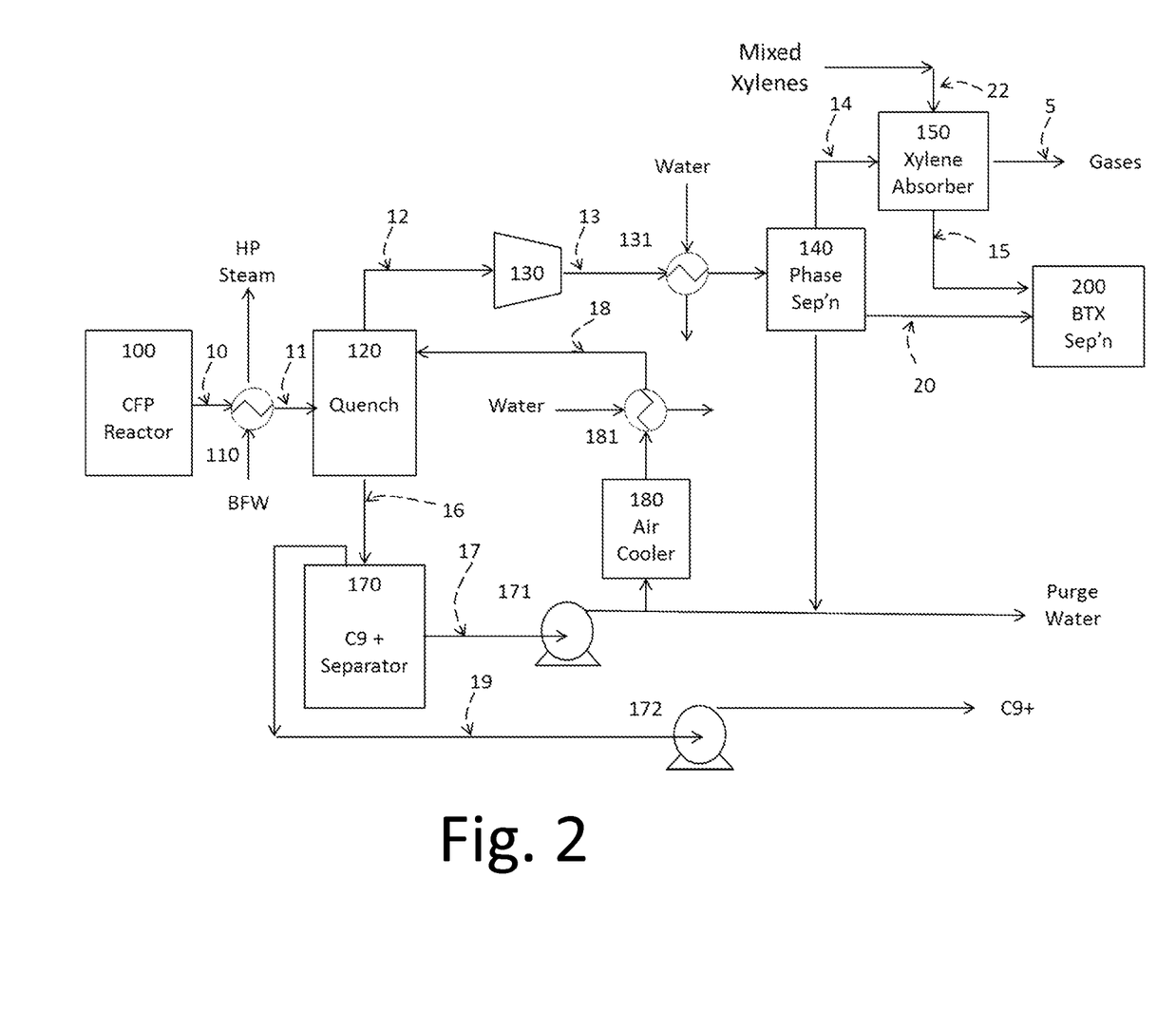
FIG. 2 presents a schematic of a recovery and quench system for BTX recovery from CFP of biomass

FIG. 2 presents a schematic of a quench and recovery system for producing benzene, toluene, xylenes, oxygenates, and C9+ products from a biomass CFP process. In FIG. 2 the CFP reactor 100 produces a product stream at a high temperature that is cooled in heat exchanger 110 and sent to a quench system 120. The raw product effluent is passed through at least one cyclone (see FIG. 1) that removes much of the solids in the mixture. In one option a venturi scrubber is placed upstream of the quench system to remove additional particulates including char, coke, catalyst, and ash. The quench system 120 contacts a stream of water with the gaseous product stream. This quenching water may comprise reaction product water made by pyrolysis and catalytic conversion of biomass. Optionally the quench water may comprise clean make-up water. Optionally, the quench water may contain corrosion inhibitors such as amines, alkanolamines, imidazoline, phosphated ethoxylated alcohols/benzotriazole derivatives, or any other material that reduces metal corrosion, The pH of the quenching water may be controlled by the addition or removal of acids, bases, or buffer solutions to achieve a desired pH. Optionally, an organic product stream from the process may be recycled to the quench unit to improve process operability. The organic product stream recycled to the quench unit can be one that comprises BTX, benzene and toluene, or a mixed xylenes stream from within the process, such as those produced in the BTX separation distillation column. The product streams from the quench system 120 include: a condensed stream that comprises water and organics comprising C9+ aromatics, oxygenates, and other compounds, and solids, and a gas/vapor product stream that comprises benzene, toluene, xylenes, CO, $CO_2$, $CH_4$, $N_2$, $H_2$, C2-C4 olefins and paraffins, and other compounds. The gas/vapor product stream from quench system 120 is passed to a compressor 130 and a heat exchanger 131. Heat exchanger 131 cools the stream and condenses recoverable hydrocarbon products. This cooling and condensing can optionally be performed by air cooled, water cooled, or chilled water cooled exchangers, or some combination of these. The compressed and cooled product stream is passed to a 3-phase separator 140. The gaseous stream from 140 (Stream 14) is sent to absorber 150 in which the gases are scrubbed with a mixed-xylenes containing absorption liquid stream obtained from the BTX separation or other liquid stream recovered from the process, to recover BTX from the gases. The liquid product from 150 (Stream 15) is optionally combined with the liquid phase from 140 (Stream 20) and the combined product stream may be sent to a BTX separation unit 200 described in more detail in FIG. 3. Alternatively, liquid streams from 140 and 150 may be separately sent to the distillation unit 210 in FIG. 3. The gas stream from absorber 150 that comprises the lighter components and fixed gases (CO, $CO_2$, $H_2$, $CH_4$, $N_2$, C2-C4 olefins and alkanes, etc.) is in part sent back to the reactor to fluidize the catalyst and provide a source of reactive olefins which can react in the presence of biomass to produce additional aromatic product. Any gas in excess of reactor fluidizing and olefin reaction requirements can be used for other processing needs, combusted, or purged. The aqueous stream from phase separator 140 is sent to the water purge stream. The water and high boiling point components from quench system 120 are sent to an aqueous/organics separator 170. Optionally a surfactant emulsion breaking compound such as an amine, amyl-, butyl-, or nonyl resin, ester, polyol, polyol ester, sulfonate, or other material as commercially available from Weatherford or Nalco may be added to the quench system liquid products. The organics phase from 170 that comprises C9+ aromatics (Stream 19) is pumped by pump 172 and sent to storage or a portion may be used in the process. The water phase (Stream 17) from 170 is pumped in pump 171 and a portion of the stream is passed through optional air cooler 180, heat exchanger 181, and recycled to the quench system. Optionally, a portion of aqueous stream 17 can be fed to a stripper column (not shown) to recover dissolved hydrocarbon materials which can be recycled back to the absorber tower 150 or recovered. Filters (not shown) can be placed after separator 170 or at other locations in the flow scheme to remove particulates, char, ash, and catalyst fines not collected in the C9+ separator from the organic and water streams. The remainder of the water is purged from the system and sent to water treatment.

Venturi scrubbers are known in the art, and typically a venturi scrubber consists of three sections: a converging section, a throat section, and a diverging section. The inlet gas stream enters the converging section and, as the area decreases, gas velocity increases. Liquid is introduced either at the throat or at the entrance to the converging section. The inlet gas moves at extremely high velocities in the small throat section producing turbulence, which causes break-up of the liquid into an enormous number of small drops. The small drops intercept and coalesce with the small, entrained particulates, tar, char, ash, coke and catalyst fines in the gas stream. The inlet streams then exit through the diverging section, where it is forced to slow down. The liquid and particulates are collected in a collection vessel downstream of the venturi and the vapors exit from the top of the collection vessel. As one non-limiting example, venturi systems are described in U.S. Pat. No. 5,279,646, which is incorporated herein by reference.

Stream 20 from phase separator 140 comprises benzene, toluene, and xylenes (collectively BTX). The composition of the BTX stream 20 comprises at least 50%, or at least 65%, or at least 75%, or at least 85%, or from 65 to 99%, or from 75 to 95%, or from 80 to 92%, or from 85 to 90% by mass BTX. The water content of the BTX stream 20 is less than 10%, or less than 5%, or less than 1%, or less than 0.5%, or less than 0.25%, or from 0.01 to 0.5%, or from 0.05 to 0.25%, or from 0.10 to 0.20% by mass. The oxygenates in the BTX stream 20 comprises less than 5%, or less than 2%, or less than 1%, or less than 0.25%, or from 0.01 to 5%, or from 0.03 to 2%, or from 0.05 to 1% by mass.

Stream 19 from separation unit 170 comprises a C9+ aromatics-containing product stream. The product stream 19 comprises at least 80%, at least 85%, at least 90%, or at least 95%, or from 60 to 99.8%, or from 80 to 99.8%, or from 90 to 99.8% aromatics by mass. The product stream 19 comprises at least 70%, or at least 75%, or at least 80%, or at least 85%, or from 70 to 99%, or from 75 to 95%, or from 80 to 90% C9+ aromatics by mass. The product stream 19 comprises at least 40%, or at least 50%, or at least 60%, or from 40 to 90%, or from 50 to 80%, or from 60 to 70% naphthalene by mass. The product stream 19 comprises at least 40%, or at least 50%, or at least 60%, or from 40 to 90%, or from 50 to 80%, or from 60 to 70% polycyclic aromatics by mass. The product stream 19 comprises less than 25%, or less than 20%, or less than 15%, or less than 10%, or from 1 to 25%, or from 5 to 20% monocyclic aromatics by mass. The product stream 19 comprises less than 25%, or less than 15%, or less than 10%, or from 0.1 to 25%, or from 1 to 15%, or from 2 to 10% oxygenates by mass. The product stream 19 comprises less than 5%, or less than 3%, or less than 1.5%, or less than 1%, or from 0.001 to 5%, or from 0.01 to 3%, or from 0.05 to 1.5%, or from 0.1 to 1% water by mass.

Stream 17 from separator 170 comprises a water product or water recycle stream, or both. Stream 17 comprises at least 85%, or at least 90%, or at least 95% water by mass. Stream 17 comprises less than 10%, or less than 5%, or less than 3%, or less than 2%, or from 0.1 to 10%, or from 0.5 to 5%, or from 1 to 3% aromatics by mass. Stream 17 comprises less than 10%, or less than 5%, or less than 2%, or less than 1%, or from 0.05 to 10%, or from 0.1 to 5%, or from 0.5 to 3% oxygenates by weight. Stream 17 comprises less than 2%, or less than 1%, or less than 0.1%, or less than 0.05%, or from 0.0001 to 2%, for from 0.0005 to 1%, or from 0.001 to 0.1% BTX by mass.

The pH of the water used for the quench unit 120 may be controlled by the addition or removal of acids, bases, or buffer solutions to achieve a desired pH. The pH can be at least 1.0, or at least 2.0, or at least 3.0, or at least 4.0, or at least 5.0, or at least 6.0, or at least 7.0, or at least 8.0, or at least 9.0, or at least 10.0, or at least 11.0, or less than 2.0, or less than 3.0, or less than 4.0, or less than 5.0, or less than 6.0, or less than 7.0, or less than 8.0, or less than 9.0, or less than 10.0, or less than 11.0. The pH of the quench water can be adjusted and controlled by addition of acids, or bases, or buffer solutions as required to meet the desired pH. Acid materials derived from the process can be used to control the pH of the quench water.

Figure 3:
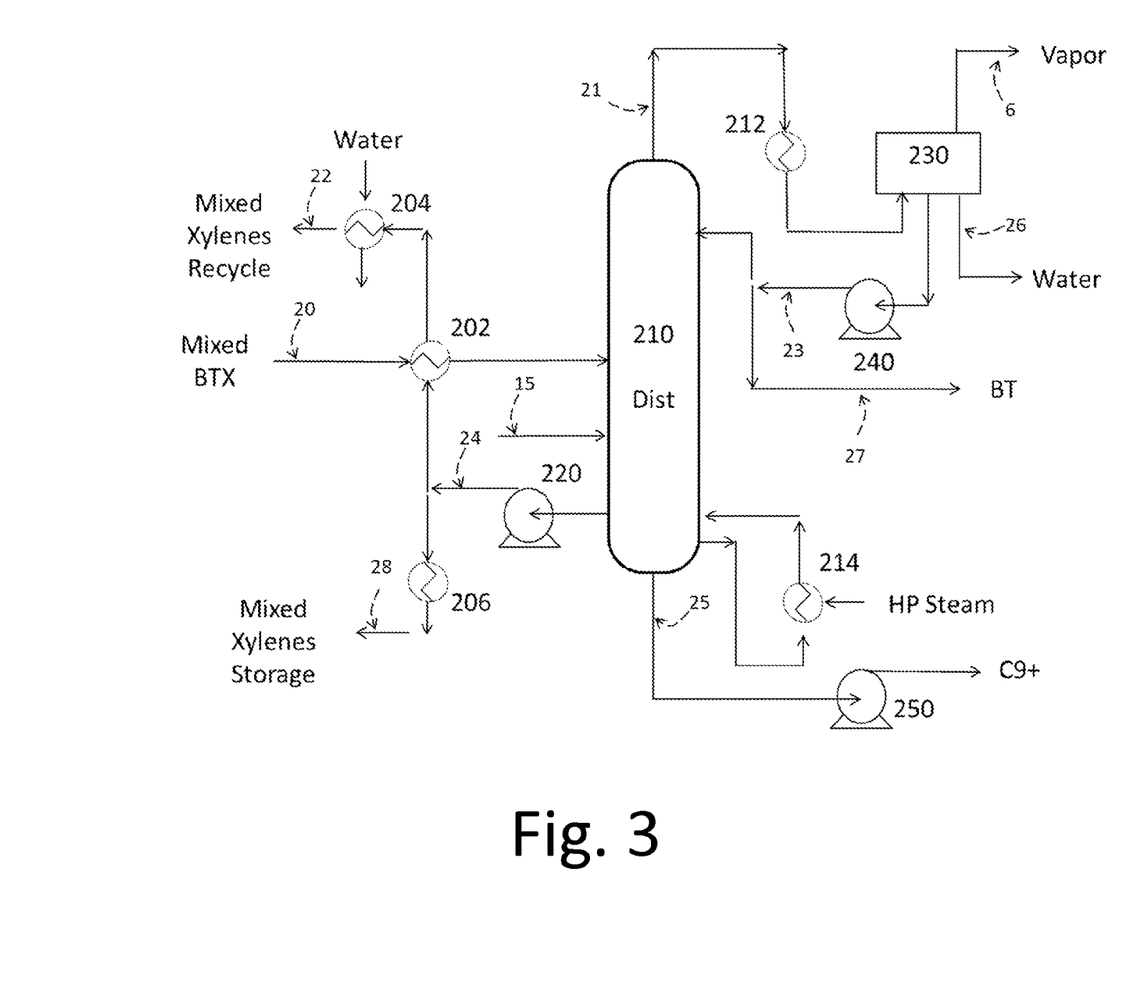
FIG. 3 presents a schematic of a BTX separation process

FIG. 3 summarizes the separation scheme for separating benzene and toluene (BT) from xylenes (X). The mixed BTX stream from the recovery system in FIG. 3 is heated with hot mixed-xylenes product or otherwise in heat exchanger 202 and then fed to distillation column 210. Stream 15 that comprises the liquid stream from absorber 150 in FIG. 2 is also fed to distillation column 210, optionally after being heated. In one embodiment stream 15 and stream 20 from FIG. 2 are combined for introduction to the distillation column. Distillation column 210 is heated by reboiling a take-off stream with high pressure steam although other methods such as reboiling with a natural gas fired furnace are envisioned as being within the scope of this invention. A light fraction of product that comprises a BT mixture is passed to condenser 212 and the condensed liquids are collected in collector 230. This lighter fraction can optionally be air cooled, water cooled, or chilled water cooled, or some combination of these. A fraction of the condensed liquids are returned to the distillation column 210 via pump 240 and the remainder of the BT stream is sent to storage for further purification. The overhead vapors from the BT condensation are combusted in a CO furnace boiler to generate steam, or optionally sent to a gas turbine to generate electricity in a combined cycle scheme, or sent to a thermal oxidizer or flare, or can be employed in the CFP process, or can be sent to a downstream process for further recovery of products or used elsewhere. The condensed aqueous phase that collects in collector 230 is sent to water treatment. A portion of the xylenes rich fraction is pumped via pump 220 from distillation column 210 to heat the incoming crude BTX mixture, cooled in heat exchanger 204 and sent to the absorber 150 in FIG. 2. The remainder of the xylenes rich fraction is sent to storage and further purification. The bottom ends from distillation column 210 are heat exchanged to raise steam (not shown), optionally cooled, and pumped via pump 250 to storage or further upgraded.

Absorber 150 in FIG. 2 may be a conventional absorber system known to those skilled in the art. The absorber can be a packed bed absorber. A preferred absorber solvent is a mixed-xylenes stream. When a mixed-xylenes stream is used as the absorber fluid the absorber is operated at a relatively low operating temperature of from −20 to 50 C, or from −5 to 30 C, or most preferably from 5 C to 10 C. The absorber is operated at elevated pressure from 100 kPa to 7000 kPa, or from 200 kPa to 7000 kPa, or most preferably the pressure of this absorption step is less than 1500 kPa, or less than 1200 kPa, or less than 1000 kPa. The feed ratio of liquid mixed xylenes to vapors for absorber 150 can range from 0.001 to 2, or from 0.002 to 1, or from 0.005 to 0.5, or more preferably from 0.01 to 0.1, or less than 0.1, or less than 0.05, or less than 0.02 on a molar basis, ie moles of mixed xylenes divided by moles of vapor. Distillation column 210 may be a conventional distillation column or a divided wall column as is known to those skilled in the art, which contains at least 5 or at least 10 or at least 20 or at least 30, or at least 50 theoretical plates or stages of distillation.

The quench system described herein has a variety of advantages in recovering products from a CFP process. The quench cools the product vapors and condenses reaction product water along with heavy aromatics, and oxygenates. The whole product inlet temp to the quench system can range from 200 to 620 C, or from 400 to 550 C, or preferably from 425 to 500 C The ratio of water to gas feed can range from 0.1:1 to 100:1 by weight, or from 0.5:1 to 20:1 by weight or from 1:1 to 10:1 by weight, or from 2:1 to 5:1 by weight. Quenching with water removes the great majority of the heavy C9+ hydrocarbons, oxygenates such as phenol and cresol, allowing further downstream vapor processing by cooling which is not otherwise possible due to the high melting point of some components of the C9+ material, e.g., naphthalene, m.p. 80° C. In some embodiments of this invention the temperature of the overhead vapor stream 12 from the quench system 120 in FIG. 2 is from 10° C. to 200° C., or from 20° C. to 150° C., or from 30° C. to 100° C., or from 40° C. to 80° C., or from 50° C. to 70° C. The overhead pressure of the vapor stream from the quench system can range from 100 kPa to 4000 kPa, or from 150 kPa to 1500 kPa, or from 200 kPa to 1000 kPa, or from 300 kPa to 700 kPa. The overhead vapor from the quench contains most of the aromatics. This vapor can then be processed further to recover BTX and other aromatic compounds.

The quench also functions as a water wash that removes particulate material such as char, coke, ash, tar and catalyst fines that carry over from the reactor cyclones. These particles may collect in the liquid phase and can be removed from the system by gravity separation, filtration or other downstream process steps known to those skilled in the art. The collected solids can optionally be returned to the catalyst regeneration step or can be collected for separation and recovery of valuable components. Removal of fine particulates in the water quench system protects other downstream equipment from damage, particularly the recycle compressor. Another advantage is that the water needed for the quench can be generated in the process when it is operating at steady state rendering the process independent of water sources other than water needed for startup.

Optionally a preliminary quench that uses an organic quench fluid is conducted upstream of the water quench. In the preliminary quench the quench fluid comprises an organic phase in which most of the material has a higher boiling point than the BTX materials, i.e. at least 140 C. The fraction of the organic quench fluid that boils at temperatures above 140 C is at least 50, or at least 60, or at least 70, or at least 80, or at least 90, or at least 95, or at least 97, or at least 99% by weight of the organic quench fluid. The organic quench fluid comprises fluids chosen from among naphtha, C9+ organics, oxygenates, product streams from the CFP process, benzene, toluene, xylenes, ethyl benzene, styrene, cumene, propyl benzene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, naphthalene, methyl-naphthalene (e.g., 1-methyl naphthalene), anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, dimethyl-hydrindene, phenol, o-cresol, m-cresol, p-cresol, catechol, resorcinol, hydroquinone, 1-naphthol, 2-naphthol, and benzofuran or combinations thereof. The organic quench fluid comprises at least 25, or at least 40, or at least 50, or at least 65 or at least 80% by weight aromatic compounds. The organic quench fluid may comprise a portion of one or more product streams of the CFP process, e.g. stream 25 of FIG. 3 or stream 19 of FIG. 2 or some combination of these. The organic quench fluid may comprise less than 50, or less than 40, or less than 30, or less than 20 or less than 10, or less than 5, or less than 2% by weight water. The organic quench fluid may be a two phase mixture of an organic phase and an aqueous phase, or an emulsion of organic and aqueous phases. The quench fluid may comprise diesel fuel, pyrolysis oil, pygas (pygas is a naphtha-range product with a high aromatics content produced in high temperature naphtha cracking during ethylene and propylene production), jet fuel, heavy cycle oils, heavy coker gas oils, heavy visbreaking distillates, heavy thermal cracking distillates clarified catalytic cracking decant oils, vacuum gas oil, intermediate and heavy vacuum distillates, naphthenic oils, heavy hydrocracker distillates, heavy distillates from hydroprocessing, or the like, or combinations thereof. In some embodiments the organic quench fluid comprises organic materials from a conventional petroleum refinery. Preferably the organic quench fluid comprises at least 10, or at least 25, or at least 50, or at least 75, or at least 90% by weight of materials produced from biomass.

In some embodiments the stream produced in the optional organic quench is passed directly into the water quench. In other embodiments the product stream is separated into a vapor and a liquid stream and only the vapor stream is passed into the water quench. In one embodiment the liquid stream produced in and separated from the organic quench is passed into the recovery section as in stream 12 in FIG. 2. In another embodiment the liquid stream produced in and separated from the organic quench is passed into a 3-phase separator as in unit 140 in FIG. 2 wherein vapor, organic liquid, and aqueous streams are separated. In some embodiments at least a portion of the organic liquid phase separated in the 3-phase separator is recycled for use as a portion of the organic quench liquid. In some embodiments the vapor phase from the 3-phase separator is passed to the xylene absorber, 140, in FIG. 2.

A preferred embodiment of the present invention employs a mixed-xylenes stream in the product recovery. Another preferred embodiment uses an absorbent fluid (solvent) that is a stream already present in the process such as xylenes, naphthalenes, C9+ mixtures, or some combination of these, thus requiring no new solvent to be introduced to the process. In another embodiment the compressed and cooled stream exiting heat exchanger 131 enters absorber 150 directly without the use of a separate 3-phase separator 140. In this case absorber 150 functions to separate the 3 phases as well as absorb aromatic compounds from the vapor into the organic liquid phase. A stream from the BTX column such as the mixed-xylene side-stream cut can serve the purpose of generating the solvent, or it can be recovered from the C9+/water separator, and therefore there is no need for a solvent extraction/recovery system. Use of a stream that is already present in the process and recovery scheme provides significant economic advantages and renders the process independent of solvent supply other than at start-up.

Optionally, a solvent other than the xylenes stream shown in FIGS. 2 and 3 can be used to recover the BTX products from the quenched product vapors. Other potential solvents include mixtures of hydrocarbon compounds such as stream 19, 22, or 25, or fractions thereof, or any solvent derived from the process that has a higher boiling point than benzene and toluene and dissolves the aromatics. In some embodiments, the product recovery solvent stream may comprise materials chosen from among benzene, toluene, xylenes, ethyl benzene, styrene, cumene, propyl benzene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, naphthalene, methyl-naphthalene (e.g., 1-methyl naphthalene), anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, dimethyl-hydrindene, phenol, o-cresol, m-cresol, p-cresol, catechol, resorcinol, hydroquinone, 1-naphthol, 2-naphthol, and benzofuran, or combinations thereof. In some embodiments, the contacting solvent may comprise paraffins, aromatics, cycloparaffins, diesel fuel, jet fuel, or combinations of these.

The CFP process may be conducted at a temperature of 400° C. or more, and the product stream from 100 in FIG.

1 is typically at a temperature of 300-620° C., or 400-575° C., or 500-550° C., and a pressure of 100 kPa to 4000 kPa, or 200 kPa to 1000 kPa, or 300 kPa to 700 kPa, or at least 200 kPa, or at least 300 kPa or at least 400 kPa. (Pressures are expressed as absolute pressures.) The raw product stream from 100 comprises aromatics, olefins, oxygenates, paraffins, $H_2$, $CH_4$, CO, $CO_2$, water, char, ash, coke, catalyst fines, and a host of other compounds. On a water-free and solids-free basis the raw product stream can comprise 20 to 60%, or 25 to 55% or 30 to 50%, or at least 20%, or at least 25%, or at least 30% CO calculated on a mass % basis. On a water-free and solids-free basis the raw product stream can comprise 10 to 50%, or 15 to 40%, or 20 to 35%, or at least 5%, or at least 10%, or at least 15%, or at least 20% $CO_2$ calculated on a mass % basis. On a water-free and solids-free basis the raw product stream can comprise 0.1 to 2.0, or 0.2 to 1.5, or 0.3 to 0.75, or at least 0.1%, or at least 0.2%, or at least 0.3%, or less than 10%, or less than 5%, or less than 1% $H_2$ calculated on a mass % basis. On a water-free and solids-free basis the raw product stream can comprise 2 to 15, or 3 to 10, or 4 to 8%, or less than 15%, or less than 10%, or less than 8% $CH_4$ calculated on a mass % basis. On a water-free and solids-free basis the raw product stream can comprise 2 to 40, or 3 to 35 or 4 to 30%, or less than 40%, or less than 35%, or less than 30%, or less than 20% BTX calculated on a mass % basis. On a water-free and solids-free basis the raw product stream can comprise 0.1 to 10%, or 0.2 to 5%, or 0.3 to 3%, or less than 5%, or less than 3%, or less than 2% oxygenates calculated on a mass % basis. On a water-free and solids-free basis the raw product stream can comprise 1 to 15%, or 2 to 10%, or 3 to 6% C2-C4, or at least 1%, or at least 2%, or at least 3% olefins calculated on a mass % basis. On a water-free and solids-free basis the raw product stream can comprise a vapor mixture where the sum of CO and $CO_2$ is from 30 to 90, or from 40 to 85, or from 50 to 80%, calculated on a mass % basis.

The quench water enters the quench system 120 at a temperature from −5 to 100° C., or 20 to 60° C., or 30 to 55° C., or 35 to 50° C. Heat exchanger 110 typically cools the raw product stream to a temperature of 250 to 600° C., or 350 to 550° C., or 400 to 500° C. The quenched, compressed, cooled product stream from heat exchanger 131 in FIG. 1 can be separated in phase separator 140 held at a temperature of −30 to 60° C., or −15 to 40° C., or −5 to 30° C., or 0 to 10° C., and pressure from 100 to 8000 kPa, or to from 500 to 4000 kPa, or from 600 to 2000 kPa. The organic vapor phase from separator 140 is contacted with a xylenes (or other solvent) stream in absorber 150 at a temperature −30 to 60° C., or −15 to 40° C., or −5 to 30° C., or 0 to 10° C., and pressure from 100 and 7000 kPa, or to from 300 to 4000 kPa, or from 400 to 1000 kPa.

The crude BTX stream is heated by heat exchange against a mixed xylenes stream in 202 in FIG. 3 where the BTX stream enters at a temperature from −10 to 150° C., or 0 to 50° C., or 2 to 20° C. and the mixed xylenes stream enters at a temperature from 50 to 300° C., or 100 to 225° C., or 150 to 200° C. to be passed to the distillation step 210.

The distillation of the BTX rich stream in 210 can be accomplished by conventional methods using conventional distillation equipment such as tray, bubble cap, packed columns, divided wall columns or the like. Distillation may be carried out at subatmospheric pressures or at atmospheric pressures or at higher pressures. Ordinarily, this distillation will be carried out at pressures from 1 to 1,000 kPa, or from 10 to 500 kPa, with pressures from 100 to 400 kPa being preferred.

The benzene and toluene (collectively BT) rich stream 27 that is a product stream of the process. Stream 27 can comprise at least 80%, at least 85%, at least 90%, at least 92%, or from 80 to 99%, or from 85 to 97%, or from 90 to 95% BT by weight. Stream 27 can comprise at least 25%, or at least 30%, or at least 35%, or from 25 to 70%, or from 30 to 60%, or from 35 to 50% benzene by weight. Stream 27 can comprise at least 30%, or at least 35%, or at least 40%, or from 30 to 80%, or from 35 to 70%, or from 40 to 60% toluene by weight. Stream 27 comprises less than 2%, or less than 1%, or less than 0.5% oxygenates by weight, or less than 0.1% oxygenates.

The product stream 28 comprises a mixed xylenes product stream. Stream 28 can comprise at least 50%, or at least 60%, or at least 70%, or from 50 to 95%, or from 60 to 90%, or from 70 to 85% xylenes (p-, o-, and m-xylenes) by weight. Product stream 28 can comprise less than 25%, or less than 20%, or less than 15%, or less than 12%, or from 1 to 25%, or from 3 to 20%, or from 5 to 15% benzene plus toluene by weight. Product stream 28 can comprise less than 20%, or less than 15%, or less than 10%, or from 0.1 to 20%, or from 1 to 15%, or from 5 to 10% naphthalene by weight.

The overhead mixed BT stream is further separated downstream in another fractionation column (not shown), or the benzene and toluene can be separated in this column if the configuration allows it, for example if it is a divided wall column. The BTX separation column 210 functions as a xylene stripper as well as a fractionator. Mixed xylenes leave the bottom of the column for further separation into para-, meta-, and ortho-xylene. Conventional processes for separating the isomers of xylene are known to those skilled in the art. The processes of the present invention provide for efficient recovery of the various components of the raw CFP product stream. The recovery of benzene in the inventive process is greater than 75, or greater than 85, or greater than 90, or greater than 95, or greater than 97%, or from 75 to 99%, or from 90 to 98%, or from 95 to 97.5% of the benzene in the raw product. The recovery of toluene in the inventive process is greater than 75, or greater than 85, or greater than 90, or greater than 95, or greater than 97%, or from 75 to 99%, or from 90 to 98.5%, or from 95 to 98% of the toluene in the raw product. The recovery of xylenes in the inventive process is greater than 75, or greater than 85, or greater than 90, or greater than 92%, or from 75 to 99%, or from 85 to 98%, or from 90 to 93% of the xylenes in the raw product. The recovery of the sum of ethylbenzene, styrene, and cumene in the inventive process is greater than 70, or greater than 80, or greater than 85, or greater than 89%, or from 70 to 99%, or from 85 to 95%, or from 88 to 90% of the ethylbenzene, styrene, and cumene in the raw product. The recovery of naphthalene in the inventive process is greater than 85, or greater than 90, or greater than 95, or greater than 97, or greater than 99%, or from 85 to 100%, or from 95 to 99.9%, or from 99 to 99.8% of the naphthalene in the raw product. The recovery of each of these products is calculated as the sum of the materials recovered in streams 20, 25, and 27 in FIG. 3.

Example 1

The recovery and separation of a typical raw process stream was modeled in an ASPEN™ model following the schemes of FIGS. 2 and 3. In the model the input rate was 211,652 kg/hr of raw product from a CFP process with solids not included. The stream compositions, temperatures, and pressures were calculated as shown in Table 1 for the process depicted in FIG. 2. The stream compositions, temperatures, and pressures were calculated as shown in Table 2 for the process depicted in FIG. 3 except heat exchanger 202 was omitted from the modeling.

The recovery of benzene is calculated to be 97.3% of the benzene in the raw product stream. The recovery of toluene is calculated to be 97.9% of the toluene in the raw product stream. The recovery of xylenes is calculated to be 92.9% of the xylenes in the raw product stream. The recovery of styrene, ethylbenzene, and cumene is 89.5%, the recovery of naphthalene is 99.8%, and the recovery of indene is 95.5% of each of these materials in the raw product. The recoveries of benzofuran, aniline, indole, indene, naphthalene, 2-methylnaphthalene, phenol, and m-cresol are 43.0%, 39.7%, 41.3%, 99.5%, 99.9%, 48.2%, 17.4%, 42.6%, respectively, of these materials in the raw product stream.

The results from the Example show that high recovery rates of benzene, toluene, xylenes, ethylbenzene, cumene, styrene, naphthalene, and oxygenates can be obtained by the process of the present invention that also removes and collects tar, solid ash, char, catalyst, and coke.

High recovery efficiencies for BTX from a complex raw product stream that contains very low concentrations of benzene, toluene, and xylenes is a surprising aspect of this invention. Separation and recovery of the BTX components from the non-condensable gases, water, heavy products, oxygenates, nitrogenates, and olefins would normally be expected to be plagued by significant losses of the desired materials due to their low concentrations and high vapor pressures. The novel arrangement of unit operations and process conditions facilitates the recovery of BTX with minimal losses.

The use of a venturi scrubber to simultaneously remove particulates and unwanted condensable components from the product stream of a biomass pyrolysis process provides superior results in the separation of BTX. Current practice in the bio-oil and aromatics production industry does not use a venturi for such a purpose. Common industrial use of venturi scrubbers is to remove particulates and toxic fumes from gas streams for pollution control. In those conventional applications, the gas stream to be cleaned contains non-condensable vapors. The ability of a venturi scrubber to simultaneously remove particulates, tars and separate other heavy hydrocarbons in a biomass to bio-oil or aromatics process is a unique and surprising aspect of the invention.

Operation of the scrubber within a narrow temperature range provides enhanced aromatic recovery and C9+ rejection. Recovery of low boiling components from a biomass pyrolysis mixture such as the raw product stream of CFP is limited due to the high vapor pressure of these materials and their tendency to distribute into both vapor and liquid organic phases. Operation of a quench or condensation tower with an overhead exit temperature that is too high permits substantial portions of higher boiling materials and water to be passed along with the desired BTX products into the recovery train causing the recovery train to be much larger and less efficient. Operation of a quench or condensation tower with an overhead exit temperature that is too low traps a significant fraction of the desired products with the quench liquid, thus removing them from the recovery train and reducing their recovery efficiency. It is surprising that the overhead temperature of the quench unit can be adjusted to increase the removal of the heavier components without losing a significant fraction of the desired BTX products, and yet the process stream has a low content of water and heavy products.

It is surprising that the BTX vapors in the overhead vapor stream comprising primarily CO, $CO_2$, and $CH_4$ from the organics/aqueous phase separator can be recovered using a stream of xylenes from the process and still achieve a high recovery of xylenes. Conventional processes use high boiling aromatic and other solvents in absorbers. In some preferred applications of the present invention, the pressure of this absorption step is at 1500 kPa or below, or 1200 kPa or below, or 1000 kPa or below, in some embodiments, the pressure is only about 900 kPa (135 psig, 9 bar), and, at any of these pressures, the gas stream from which BTX are to be recovered contains at least 60% (CO+CO2), or at least 70%, or at least 80% and in some embodiments, 70 to 95%, or 80% to 90% (CO+CO2) in addition to $H_2$, $C_1$-$C_4$ hydrocarbons, benzene, toluene, and traces of xylenes and water. Under these conditions, it is surprising that xylene would effectively recover BTX from the product stream. It is surprising that recycling BTX or some portion of BTX to the quench unit improves operability of the unit without significant reduction of the recovery of BTX from the process.

TABLE 1

Stream concentrations in weight % and properties for Example 1. Stream labels refer to FIG. 2.

| Stream label in FIG. 3 | 10 | 11 | 12 | 16 | 17 | 18 | 19 | 13 | 20 | 14 | 22 | 15 | 5 |
|---|---|---|---|---|---|---|---|---|---|---|---|---|---|
| Pressure, kPa | 441 | 401 | 371 | 371 | 371 | 391 | 371 | 1101 | 901 | 901 | 1001 | 850 | 801 |
| Temperature, C. | 578 | 475 | 56 | 115 | 115 | 40 | 115 | 164 | 5 | 5 | 5 | 6 | 8 |
| H2 | 0.41 | 0.41 | 0.51 | 0.00 | 0.00 | 0.00 | 0.00 | 0.51 | 0.00 | 0.58 | 0.00 | 0.00 | 0.59 |
| CO | 36.16 | 36.16 | 45.10 | 0.07 | 0.07 | 0.07 | 0.03 | 45.10 | 1.15 | 51.50 | 0.00 | 1.01 | 51.96 |
| CO2 | 25.44 | 25.44 | 31.63 | 0.44 | 0.44 | 0.44 | 0.39 | 31.63 | 5.78 | 35.49 | 0.00 | 4.94 | 35.53 |
| CH4 | 4.98 | 4.98 | 6.20 | 0.01 | 0.01 | 0.01 | 0.02 | 6.20 | 0.49 | 7.06 | 0.00 | 0.48 | 7.10 |
| Propane | 0.08 | 0.08 | 0.10 | 0.00 | 0.00 | 0.00 | 0.00 | 0.10 | 0.06 | 0.11 | 0.00 | 0.05 | 0.10 |
| Ethylene | 2.08 | 2.08 | 2.59 | 0.00 | 0.00 | 0.00 | 0.03 | 2.59 | 0.21 | 2.95 | 0.00 | 0.32 | 2.96 |
| Propylene | 0.99 | 0.99 | 1.24 | 0.00 | 0.00 | 0.00 | 0.02 | 1.24 | 0.55 | 1.36 | 0.00 | 0.53 | 1.33 |
| C4-C7 olefins | 0.11 | 0.11 | 0.14 | 0.00 | 0.00 | 0.00 | 0.01 | 0.14 | 0.62 | 0.09 | 0.00 | 0.33 | 0.06 |
| C4-C7 paraffins | 0.12 | 0.12 | 0.15 | 0.01 | 0.01 | 0.01 | 0.02 | 0.15 | 0.62 | 0.09 | 0.37 | 0.57 | 0.08 |
| Benzene | 2.51 | 2.51 | 3.13 | 0.01 | 0.00 | 0.00 | 0.65 | 3.13 | 27.13 | 0.48 | 0.00 | 7.13 | 0.00 |
| Toluene | 3.74 | 3.74 | 4.63 | 0.01 | 0.00 | 0.00 | 2.13 | 4.63 | 44.51 | 0.22 | 10.96 | 11.45 | 0.07 |
| p-Xylene | 0.46 | 0.46 | 0.56 | 0.00 | 0.00 | 0.00 | 0.94 | 0.56 | 5.54 | 0.01 | 26.58 | 21.80 | 0.05 |
| m-Xylene | 0.69 | 0.69 | 0.84 | 0.01 | 0.00 | 0.00 | 1.45 | 0.84 | 8.30 | 0.01 | 38.74 | 31.84 | 0.07 |
| o-Xylene | 0.18 | 0.18 | 0.22 | 0.00 | 0.00 | 0.00 | 0.58 | 0.22 | 2.19 | 0.00 | 10.83 | 8.98 | 0.01 |
| Ethylbenzene | 0.07 | 0.07 | 0.09 | 0.00 | 0.00 | 0.00 | 0.13 | 0.09 | 0.87 | 0.00 | 4.20 | 3.46 | 0.01 |
| Propylbenzene | 0.00 | 0.00 | 0.00 | 0.00 | 0.00 | 0.00 | 0.02 | 0.00 | 0.01 | 0.00 | 0.07 | 0.06 | 0.00 |
| Cumene | 0.06 | 0.06 | 0.07 | 0.00 | 0.00 | 0.00 | 0.33 | 0.07 | 0.74 | 0.00 | 3.77 | 3.15 | 0.00 |

TABLE 1-continued

Stream concentrations in weight % and properties for Example 1. Stream labels refer to FIG. 2.

| Stream label in FIG. 3 | 10 | 11 | 12 | 16 | 17 | 18 | 19 | 13 | 20 | 14 | 22 | 15 | 5 |
|---|---|---|---|---|---|---|---|---|---|---|---|---|---|
| 1,2,3-trimethylbenzene | 0.05 | 0.05 | 0.02 | 0.01 | 0.00 | 0.00 | 2.72 | 0.02 | 0.16 | 0.00 | 0.76 | 0.64 | 0.00 |
| Styrene | 0.05 | 0.05 | 0.06 | 0.00 | 0.00 | 0.00 | 0.20 | 0.06 | 0.58 | 0.00 | 2.87 | 2.39 | 0.00 |
| Benzofuran | 0.02 | 0.02 | 0.00 | 0.06 | 0.06 | 0.06 | 0.39 | 0.00 | 0.04 | 0.00 | 0.20 | 0.17 | 0.00 |
| Aniline | 0.01 | 0.01 | 0.00 | 0.03 | 0.03 | 0.03 | 0.24 | 0.00 | 0.02 | 0.00 | 0.08 | 0.06 | 0.00 |
| Indole | 0.01 | 0.01 | 0.00 | 0.03 | 0.03 | 0.03 | 0.35 | 0.00 | 0.00 | 0.00 | 0.00 | 0.00 | 0.00 |
| Indene | 0.02 | 0.02 | 0.00 | 0.01 | 0.00 | 0.00 | 1.67 | 0.00 | 0.01 | 0.00 | 0.06 | 0.05 | 0.00 |
| Naphthalene | 0.80 | 0.80 | 0.00 | 0.23 | 0.01 | 0.01 | 66.13 | 0.00 | 0.01 | 0.00 | 0.01 | 0.01 | 0.00 |
| 2-Methylnaphthalene | 0.40 | 0.40 | 0.01 | 1.15 | 1.10 | 1.10 | 15.23 | 0.01 | 0.07 | 0.00 | 0.02 | 0.02 | 0.00 |
| Phenol | 0.05 | 0.05 | 0.00 | 0.23 | 0.23 | 0.23 | 0.57 | 0.00 | 0.03 | 0.00 | 0.15 | 0.12 | 0.00 |
| m-Cresol | 0.17 | 0.17 | 0.01 | 0.53 | 0.51 | 0.51 | 5.20 | 0.01 | 0.10 | 0.00 | 0.33 | 0.28 | 0.00 |
| Water | 20.32 | 20.32 | 2.69 | 97.15 | 97.48 | 97.48 | 0.58 | 2.69 | 0.16 | 0.07 | 0.00 | 0.13 | 0.06 |
| TOTAL | 100.00 | 100.00 | 100.00 | 100.00 | 100.00 | 100.00 | 100.00 | 100.00 | 100.00 | 100.00 | 100.00 | 100.00 | 100.00 |

TABLE 2

Stream concentrations in weight % and properties for Example 1. Stream labels refer to FIG. 3.

| Stream label in FIG. 4 | 20 | 15 | 23 | 21 | 24 | 25 | 6 | 26 | 27 | 28 | 22 |
|---|---|---|---|---|---|---|---|---|---|---|---|
| Pressure, kPa | 901 | 850 | 201 | 306 | 315 | 420 | 201 | 201 | 201 | 1101 | 1101 |
| Temperature, C. | 5 | 6 | 5 | 135 | 183 | 242 | 5 | 5 | 5 | 60 | 60 |
| H2 | 0.00 | 0.00 | 0.00 | 0.00 | 0.00 | 0.00 | 0.00 | 0.00 | 0.00 | 0.00 | 0.00 |
| CO | 1.15 | 1.01 | 0.11 | 0.72 | 0.00 | 0.00 | 16.95 | 0.28 | 0.11 | 0.00 | 0.00 |
| CO2 | 5.78 | 4.94 | 3.10 | 5.28 | 0.00 | 0.00 | 63.57 | 1.99 | 3.11 | 0.00 | 0.00 |
| CH4 | 0.49 | 0.48 | 0.13 | 0.37 | 0.00 | 0.00 | 6.83 | 0.03 | 0.13 | 0.00 | 0.00 |
| Propane | 0.06 | 0.05 | 0.07 | 0.08 | 0.00 | 0.00 | 0.38 | 0.10 | 0.07 | 0.00 | 0.00 |
| Ethylene | 0.21 | 0.32 | 0.06 | 0.19 | 0.00 | 0.00 | 3.63 | 0.00 | 0.06 | 0.00 | 0.00 |
| Propylene | 0.55 | 0.53 | 0.52 | 0.66 | 0.00 | 0.00 | 4.56 | 0.01 | 0.52 | 0.00 | 0.00 |
| C4-C7 olefins | 0.62 | 0.33 | 0.96 | 0.94 | 0.00 | 0.00 | 0.44 | 0.21 | 0.96 | 0.00 | 0.00 |
| C4-C7 paraffins | 0.62 | 0.57 | 0.82 | 0.80 | 0.37 | 0.01 | 0.46 | 0.32 | 0.82 | 0.37 | 0.37 |
| Benzene | 27.13 | 7.13 | 38.80 | 37.46 | 0.00 | 0.00 | 2.12 | 0.07 | 38.85 | 0.00 | 0.00 |
| Toluene | 44.51 | 11.45 | 54.48 | 52.52 | 10.96 | 0.13 | 0.81 | 0.02 | 54.55 | 10.96 | 10.96 |
| p-Xylene | 5.54 | 21.80 | 0.11 | 0.11 | 26.58 | 4.93 | 0.00 | 0.00 | 0.12 | 26.58 | 26.58 |
| m-Xylene | 8.30 | 31.84 | 0.49 | 0.47 | 38.74 | 6.88 | 0.00 | 0.00 | 0.49 | 38.74 | 38.74 |
| o-Xylene | 2.19 | 8.98 | 0.02 | 0.02 | 10.83 | 3.53 | 0.00 | 0.00 | 0.02 | 10.83 | 10.83 |
| Ethylbenzene | 0.87 | 3.46 | 0.02 | 0.02 | 4.20 | 0.77 | 0.00 | 0.00 | 0.02 | 4.20 | 4.20 |
| Propylbenzene | 0.01 | 0.06 | 0.00 | 0.00 | 0.07 | 0.11 | 0.00 | 0.00 | 0.00 | 0.07 | 0.07 |
| Cumene | 0.74 | 3.15 | 0.00 | 0.00 | 3.77 | 1.86 | 0.00 | 0.00 | 0.00 | 3.77 | 3.77 |
| 1,2,3-trimethylbenzene | 0.16 | 0.64 | 0.00 | 0.00 | 0.76 | 6.55 | 0.00 | 0.00 | 0.00 | 0.76 | 0.76 |
| Styrene | 0.58 | 2.39 | 0.01 | 0.00 | 2.87 | 0.81 | 0.00 | 0.00 | 0.01 | 2.87 | 2.87 |
| Benzofuran | 0.04 | 0.17 | 0.00 | 0.00 | 0.20 | 0.85 | 0.00 | 0.00 | 0.00 | 0.20 | 0.20 |
| Aniline | 0.02 | 0.06 | 0.00 | 0.00 | 0.08 | 0.48 | 0.00 | 0.00 | 0.00 | 0.08 | 0.08 |
| Indole | 0.00 | 0.00 | 0.00 | 0.00 | 0.00 | 0.51 | 0.00 | 0.00 | 0.00 | 0.00 | 0.00 |
| Indene | 0.01 | 0.05 | 0.00 | 0.00 | 0.06 | 1.27 | 0.00 | 0.00 | 0.00 | 0.06 | 0.06 |
| Naphthalene | 0.01 | 0.01 | 0.00 | 0.00 | 0.01 | 5.20 | 0.00 | 0.00 | 0.00 | 0.01 | 0.01 |
| 2-Methylnaphthalene | 0.07 | 0.02 | 0.00 | 0.00 | 0.02 | 44.45 | 0.00 | 0.00 | 0.00 | 0.02 | 0.02 |
| Phenol | 0.03 | 0.12 | 0.00 | 0.00 | 0.15 | 0.32 | 0.00 | 0.00 | 0.00 | 0.15 | 0.15 |
| m-Cresol | 0.10 | 0.28 | 0.00 | 0.00 | 0.33 | 21.35 | 0.00 | 0.00 | 0.00 | 0.33 | 0.33 |
| Water | 0.16 | 0.13 | 0.22 | 0.27 | 0.00 | 0.00 | 0.22 | 96.95 | 0.10 | 0.00 | 0.00 |
| TOTAL | 100.00 | 100.00 | 100.00 | 100.00 | 100.00 | 100.00 | 100.00 | 100.00 | 100.00 | 100.00 | 100.00 |

What is claimed:

1. A method for producing aromatic chemicals from the product stream of a catalytic pyrolysis process, comprising:
   quenching the product stream with water;
   separating a first vapor phase and a first liquid product,
   recovering aromatics from the first vapor phase; and
   recovering oxygenates from the first liquid product.

2. The method of claim 1 wherein the catalytic pyrolysis process comprises pyrolyzing biomass and further wherein the temperature of the first vapor phase is from 10° C. to 200° C.

3. The method of claim 2 comprising:
   condensing the first vapor phase to produce a second liquid phase and a second vapor phase from the first vapor phase.

4. The method of claim 3 wherein the second liquid comprises at least 50%, or at least 65%, or at least 75%, or at least 85%, or from 65 to 99%, or from 75 to 95%, or from 80 to 92%, or from 85 to 90% by weight benzene plus toluene plus xylenes.

5. The method of claim 3 wherein the second liquid phase comprises less than 5%, or less than 2%, or less than 1%, or less than 0.25%, or from 0.01 to 5%, or from 0.03 to 2%, or from 0.05 to 1% by weight oxygenates.

6. The method of claim 1 wherein the catalytic pyrolysis process comprises pyrolyzing biomass and further comprising
- condensing the first vapor phase and separating a second liquid phase and a second vapor phase;
- contacting the first vapor phase or second vapor phase or a combination of them with a contacting solvent to produce a third liquid phase and third vapor phase,
- recovering aromatics from the second liquid phase and the third liquid phase.

7. The method of claim 6 wherein the contacting solvent comprises a liquid stream produced from biomass in the process.

8. The method of claim 1 wherein the contacting solvent comprises a portion of the first liquid product or the second liquid phase.

9. The method of claim 6 wherein the contacting solvent comprises materials chosen from among benzene, toluene, xylenes, ethyl benzene, styrene, cumene, propyl benzene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, naphthalene, methyl-naphthalene (e.g., 1-methyl naphthalene), anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, dimethyl-hydrindene, phenol, o-cresol, m-cresol, p-cresol, catechol, resorcinol, hydroquinone, 1-naphthol, 2-naphthol, benzofuran, diesel fuel, jet fuel, paraffins, aromatics, cycloparaffins, or combinations thereof.

10. The method of claim 1 wherein the first liquid product is separated into an organic fraction and an aqueous fraction.

11. The method of claim 10 wherein the organic stream comprises at least 80%, at least 85%, at least 90%, or at least 95%, or from 90 to 99.8% aromatics by weight.

12. The method of claim 10 wherein the organic stream comprises at least 40%, or at least 50%, or at least 60%, or from 40 to 90%, or from 50 to 80%, or from 60 to 70% naphthalene by weight.

13. The method of claim 1 wherein
- the first liquid product is separated into an organic fraction and an aqueous fraction, and
- a portion of the aqueous fraction is used as quench water.

14. The method of claim 6 wherein a fluidization gas of the CFP process comprises a portion of the third vapor phase.

15. The method of claim 6 wherein the first vapor is compressed before it is contacted with the contacting solvent.

16. The method of claim 6 wherein the raw product stream passes through a venturi scrubber before entering the quench system.

17. The method of claim 1 wherein, on a water-free and solids-free basis, the product stream of a catalytic pyrolysis process that is subjected to the inventive method comprises 20 to 60%, or 25 to 55% or 30 to 50%, or at least 20%, or at least 25%, or at least 30% CO calculated on a mass % basis.

18. The method of claim 1 wherein on a water-free and solids-free basis the product stream of a catalytic pyrolysis process that is subjected to the inventive method comprises 0.1 to 10, or 0.2 to 5, or 0.3 to 3%, or less than 5%, or less than 3%, or less than 2% oxygenates calculated on a mass % basis.

19. The method of claim 10 wherein the aqueous stream is fed to a stripper column to recover dissolved hydrocarbon materials.

20. A method as in claim 1 wherein a surfactant emulsion breaking compound is added to the first liquid products.

21. A method as in claim 20 wherein the surfactant emulsion breaking compound is chosen from among amines, amyl-, butyl-, or nonyl resins, esters, polyols, polyol esters, sulfonates, or other material that breaks aqueous and organic emulsions, or some combination thereof.

22. A method as in claim 1 wherein the water used for quench contains a corrosion inhibitor.

23. A method as in claim 1 wherein an organic stream comprising benzene, toluene, xylenes, or ethyl benzene, or some combination of these is fed to a quench unit.

24. The method of claim 6 wherein the contacting solvent comprises a portion of the first liquid phase.

25. The method of claim 3 wherein the first liquid product is separated into an organic fraction and an aqueous fraction, and a portion of the organic phase is used as the contacting solvent.

26. The method of claim 6 wherein the contacting solvent has a boiling point greater than the boiling point of toluene.

27. The method of claim 10 wherein at least 25%, or at least 50%, or at least 75%, or at least 90%, or at least 95% of the water used in the quench liquid is water produced from biomass in the process.

28. The method of claim 6 wherein a transport fluid used to transport biomass into the CFP reactor comprises a portion of the third vapor phase.

* * * * *